United States Patent
Meister et al.

(10) Patent No.: US 9,770,590 B2
(45) Date of Patent: Sep. 26, 2017

(54) SWITCHING HEARING IMPLANT CODING STRATEGIES

(71) Applicant: MED-EL Elektromedizinische Geraete GmbH, Innsbruck (AT)

(72) Inventors: Dirk Meister, Innsbruck (AT); Thomas Schwarzenbeck, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 15/178,768

(22) Filed: Jun. 10, 2016

(65) Prior Publication Data

US 2017/0001007 A1    Jan. 5, 2017

Related U.S. Application Data

(60) Provisional application No. 62/174,003, filed on Jun. 11, 2015, provisional application No. 62/215,187, filed on Sep. 8, 2015.

(51) Int. Cl.
*A61N 1/05*    (2006.01)
*A61N 1/36*    (2006.01)

(52) U.S. Cl.
CPC ....... *A61N 1/36032* (2013.01); *A61N 1/0541* (2013.01)

(58) Field of Classification Search
CPC .......................... A61N 1/36032; A61N 1/0541
See application file for complete search history.

(56) References Cited

U.S. PATENT DOCUMENTS

| | | |
|---|---|---|
| 6,594,525 B1 | 7/2003 | Zierhofer |
| 7,937,155 B1 | 5/2011 | Voelkel |
| 2010/0094380 A1* | 4/2010 | Dadd .................. A61N 1/0541 607/50 |

(Continued)

OTHER PUBLICATIONS

Middlebrooks, "Auditory Cortex Phase Locking to Amplitude-Modulated Cochlear Implant Pulse Trains," Journal of Neurophysiol, vol. 100, pp. 76-91, 2008.

(Continued)

*Primary Examiner* — William Levicky
(74) *Attorney, Agent, or Firm* — Sunstein Kann Murphy & Timbers LLP

(57) ABSTRACT

An input sound signal is processed to generate band pass signals. Band pass envelope signals are extracted that reflect time varying amplitude of the band pass signals. Stimulation timing signals are generated that reflect the temporal fine structure features of the band pass signals. A key feature value present in the input sound signal or the band pass signals is monitored. For one or more selected band pass signals, a stimulation coding strategy is selected from multiple possible stimulation coding strategies based on the key feature value. The multiple possible stimulation coding strategies including an envelope-based stimulation coding strategy based on the band pass envelope signals, and an event-based stimulation coding strategy based on the stimulation timing signals. The selected stimulation coding strategy is used to produce the electrode stimulation signals for the electrode contacts. The arrangement automatically switches between different selected stimulation coding strategies as a function of changes in the key feature value.

15 Claims, 15 Drawing Sheets

(56) References Cited

U.S. PATENT DOCUMENTS

2010/0198300 A1 8/2010 Smith
2014/0074183 A1 3/2014 Kulkarni et al.
2016/0106980 A1 4/2016 Sürth et al.
2016/0165363 A1 6/2016 Meister et al.

OTHER PUBLICATIONS

Wilson et al., "Better speech recognition with cochlear implants," Letters to Nature, vol. 325, pp. 236-238, Jul. 18, 1991.
International Searching Authority, International Search Report—International Application No. PCT/US16/36826, dated Sep. 6, 2016, together with the Written Opinion of the International Searching Authority, 18 pages.

* cited by examiner

SWITCHING HEARING IMPLANT CODING STRATEGIES

This application claims priority from U.S. Provisional Patent Application 62/174,003, filed Jun. 11, 2015, and from U.S. Provisional Patent Application 62/215,187, filed Sep. 8, 2015, both of which are incorporated herein by reference in their entireties.

TECHNICAL FIELD

The present invention relates to signal processing arrangements for hearing implants, and more particularly, to automatically transitioning speech coding strategies for cochlear implants.

BACKGROUND ART

As shown in FIG. 1, sounds are transmitted by a human ear from the outer ear 101 to the tympanic membrane (eardrum) 102, which moves the bones of the middle ear 103 (malleus, incus, and stapes) that vibrate the oval window and round window openings of the cochlea 104. The cochlea 104 is a long fluid-filled duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolus where the spiral ganglion cells of the acoustic nerve 113 reside. In response to received sounds transmitted by the middle ear 103, the cochlea 104 functions as a transducer to generate electric pulses which are transmitted to the cochlear nerve 113, and ultimately to the brain which perceives the neural signals as sound.

Hearing is impaired when there are problems in the ability to transduce external sounds into meaningful action potentials along the neural substrate of the cochlea 104. To improve impaired hearing, auditory prostheses have been developed. In some cases, hearing impairment can be addressed by a cochlear implant (CI), a brainstem-, midbrain- or cortical implant that electrically stimulates auditory nerve tissue with small currents delivered by multiple electrode contacts distributed along an implant electrode. For cochlear implants, the electrode array is inserted into the cochlea 104. For brain-stem, midbrain and cortical implants, the electrode array is located in the auditory brainstem, midbrain or cortex, respectively.

FIG. 1 shows some components of a typical cochlear implant system where an external microphone provides an audio signal input to an external signal processor 111 which implements one of various known signal processing schemes. For example, signal processing approaches that are well-known in the field of cochlear implants include continuous interleaved sampling (CIS) digital signal processing, channel specific sampling sequences (CSSS) digital signal processing, spectral peak (SPEAK) digital signal processing, fine structure processing (FSP) and compressed analog (CA) signal processing.

The processed signal is converted by the external signal processor 111 into a digital data format, such as a sequence of data frames, for transmission by an external coil 107 into a receiving stimulator processor 108. Besides extracting the audio information, the receiver processor in the stimulator processor 108 may perform additional signal processing such as error correction, pulse formation, etc., and produces a stimulation pattern (based on the extracted audio information) that is sent through electrode lead 109 to an implanted electrode array 110. Typically, the electrode array 110 includes multiple stimulation contacts 112 on its surface that provide selective electrical stimulation of the cochlea 104.

An audio signal, such as speech or music, can be processed into multiple frequency band pass signals, each having a signal envelope and fine time structure within the envelope. One common speech coding strategy is the so called "continuous-interleaved-sampling strategy" (CIS), as described by Wilson B. S., Finley C. C., Lawson D. T., Wolford R. D., Eddington D. K., Rabinowitz W. M., "Better speech recognition with cochlear implants," Nature, vol. 352, 236-238 (July 1991), which is hereby incorporated herein by reference. The CIS speech coding strategy samples the signal envelopes at predetermined time intervals, providing a remarkable level of speech understanding merely by coding the signal envelope of the speech signal. This can be explained, in part, by the fact that auditory neurons phase lock to amplitude modulated electrical pulse trains (see, for example, Middlebrooks, J. C., "Auditory Cortex Phase Locking to Amplitude-Modulated Cochlear Implant Pulse Trains," J Neurophysiol, 100(1), p. 76-912008, 2008 July, which is hereby incorporated herein by reference).

However, for normal hearing subjects, both signal cues, the envelope and the final time structure, are important for localization and speech understanding in noise and reverberant conditions (Zeng, Fan-Gang, et al. "Auditory perception with slowly-varying amplitude and frequency modulations." *Auditory Signal Processing*. Springer New York, 2005. 282-290; Drennan, Ward R., et al. "Effects of temporal fine structure on the lateralization of speech and on speech understanding in noise." *Journal of the Association for Research in Otolaryngology* 8.3 (2007): 373-383; and Hopkins, Kathryn, and Brian Moore. "The contribution of temporal fine structure information to the intelligibility of speech in noise." *The Journal of the Acoustical Society of America* 123.5 (2008): 3710-3710; and all of which are hereby incorporated herein by reference in their entireties).

Older speech coding strategies mainly encode the slowly varying signal envelope information and do not transmit the fine time structure of a signal. More recent coding strategies, for example, Fine Structure Processing (FSP), also transmit the fine time structure information. In FSP, the fine time structure of low frequency channels is transmitted through Channel Specific Sampling Sequences (CSSS) that start at negative to positive zero crossings of the respective band pass filter output (see U.S. Pat. No. 6,594,525, which is incorporated herein by reference). The basic idea of FSP is to apply a stimulation pattern, where a particular relationship to the center frequencies of the filter channels is preserved, i.e., the center frequencies are represented in the temporal waveforms of the stimulation patterns, and are not fully removed, as is done in CIS. Each stimulation channel is associated with a particular CSSS, which is a sequence of ultra-high-rate biphasic pulses (typically 5-10 kpps). Each CSSS has a distinct length (number of pulses) and distinct amplitude distribution. The length of a CSSS may be derived, for example, from the center frequency of the associated band pass filter. A CSSS associated with a lower filter channel is longer than a CSSS associated with a higher filter channel. For example, it may be one half of the period of the center frequency. The amplitude distribution may be adjusted to patient specific requirements.

For illustration, FIG. 2A-2B show two examples of CSSS for a 6-channel system. In FIG. 2A, the CSSS's are derived by sampling one half of a period of a sinusoid whose frequency is equal to the center frequency of the band pass filter (center frequencies at 440 Hz, 696 Hz, 1103 Hz, 1745 Hz, 2762 Hz, and 4372 Hz). Sampling is achieved by means of biphasic pulses at a rate of 10 kpps and a phase duration of 25 μs. For Channels 5 and 6, one half of a period of the center frequencies is too short to give space for more than one stimulation pulse, i.e., the "sequences" consist of only one pulse, respectively. Other amplitude distributions may be utilized. For example, in FIG. 2B, the sequences are derived by sampling one quarter of a sinusoid with a frequency, which is half the center frequency of the band pass filters. These CSSS's have about the same durations as the CSSS's in FIG. 2A, respectively, but the amplitude distribution is monotonically increasing. Such monotonic distributions might be advantageous, because each pulse of the sequence can theoretically stimulate neurons at sites which cannot be reached by its predecessors.

FIG. 3 illustrates a typical signal processing implementation of the FSP coding strategy. A Preprocessor Filter Bank 301 processes an input sound signal to generate band pass signals that each represent a band pass channel defined by an associated band of audio frequencies. The output of the Preprocessor Filter Bank 301 goes to an Envelope Detector 302 that extracts band pass envelope signals reflecting time varying amplitude of the band pass signals which includes unresolved harmonics and are modulated with the difference tones of the harmonics, mainly the fundamental frequency F0, and to a Stimulation Timing Module 303 that generates stimulation timing signals reflecting the temporal fine structure features of the band pass signals. For FSP, the Stimulation Timing Module 303 detects the negative to positive zero crossings of each band pass signal and in response starts a CSSS as a stimulation timing signal. A Pulse Generator 304 uses the band pass envelope signals and the stimulation timing signals to produce the electrode stimulation signals for the electrode contacts in the implant 305.

FSP and FS4 are the sole commercially available coding strategies that code the temporal fine structure information. Although they have be shown to perform significantly better than e.g. CIS in many hearing situations, there are some other hearing situations in which no significant benefit has been found so far over CIS-like envelope-only coding strategies, in particular with regard to localization and speech understanding in noisy and reverberant conditions.

Temporal fine structure might be more affected by noise than the envelope is. It might be beneficial to use fine structure stimulation depending, for example, on the signal of noise ratio or on the dynamic reverberation ratio. In existing coding strategies, the use of the temporal fine structure is adapted in a post-surgical fitting session and is not adaptive to the signal to noise ratio.

SUMMARY

Embodiments of the present invention are directed to systems and methods for generating electrode stimulation signals for the electrode contacts in a cochlear implant electrode array. A preprocessor filter bank is configured to process an input sound signal to generate band pass signals that each represent a band pass channel defined by an associated band of audio frequencies. An envelope detector is configured to extract band pass envelope signals reflecting time varying amplitude of the band pass signals. A stimulation timing module is configured to generate stimulation timing signals reflecting the temporal fine structure features of the band pass signals. A key feature monitor module is configured to monitor a key feature value present in the input sound signal or the band pass signals. A stimulation coding module is configured to: i. select a stimulation coding strategy for one or more selected band pass signals from a plurality of stimulation coding strategies based on the key feature value, wherein the plurality of stimulation coding strategies include: (1) an envelope-based stimulation coding strategy based on the band pass envelope signals, and (2) an event-based stimulation coding strategy based on the stimulation timing signals, and ii. switch between different selected stimulation coding strategies as a function of changes in the key feature value. The stimulation coding module is configured to autonomously select the appropriate coding strategy at each point in time. A pulse generator is configured to use the selected stimulation coding strategy to produce the electrode stimulation signals for the electrode contacts.

In specific embodiments, the stimulation coding module may be configured to switch between different selected stimulation coding strategies directly without a transition period of time, or it may switch between different selected stimulation coding strategies by adaptively changing the selected stimulation coding strategy over a transition period of time to become a different stimulation coding strategy; for example, either after or while the key feature value changes from an initial value to a coding change value. One of the stimulation coding strategies may use adaptive stimulation pulse rates and another stimulation coding strategy may use constant stimulation rates.

The key feature value may be a signal to noise ratio (SNR) or a direct to reverberation ratio (DRR) of the input sound signal; or envelope slope, envelope peak, or envelope amplitude of the band pass envelope signals. The stimulation coding module may be configured to select and switch between coding strategies for a single band pass signal, or for multiple selected band pass signals—e.g., using an n of m strategy or for a dominant channel having a largest key feature value and a plurality of adjacent neighboring channels.

DETAILED DESCRIPTION

Parameters of a given cochlear implant stimulation coding strategy might not be optimal for all listening conditions. For example, in noisy conditions some stimulation coding strategies might perform better than others since temporal fine structure typically is more affected by noise than is the band pass signal envelope. It would be beneficial to switch from one stimulation coding strategy to another, depending on listening conditions. Depending on all the specific circumstances, the switching may usefully be performed in small increments so that the transition happens in a smooth morphing from one stimulation coding strategy to the other. Alternatively, in other situations, it may be beneficial to directly switch between different stimulation coding strategies without a transition period of time. Either way, the input sound signal or the band pass signals are monitored and analyzed to estimate one or more key features that are present. Based on the key feature(s), the stimulation coding strategy is automatically modified.

Figure 1:
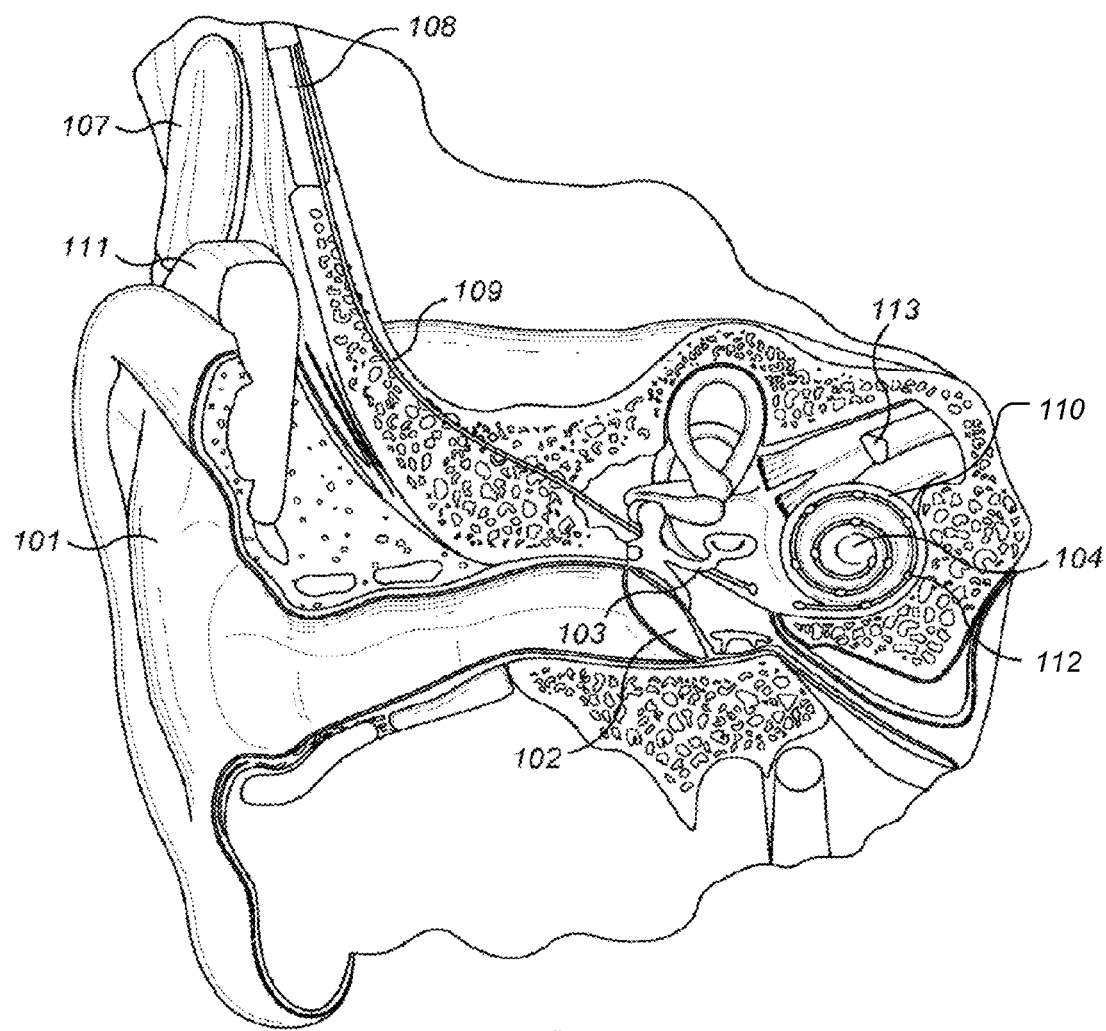
FIG. 1 shows anatomical structures of a human ear and some components of a typical cochlear implant system.
Figure 2A:
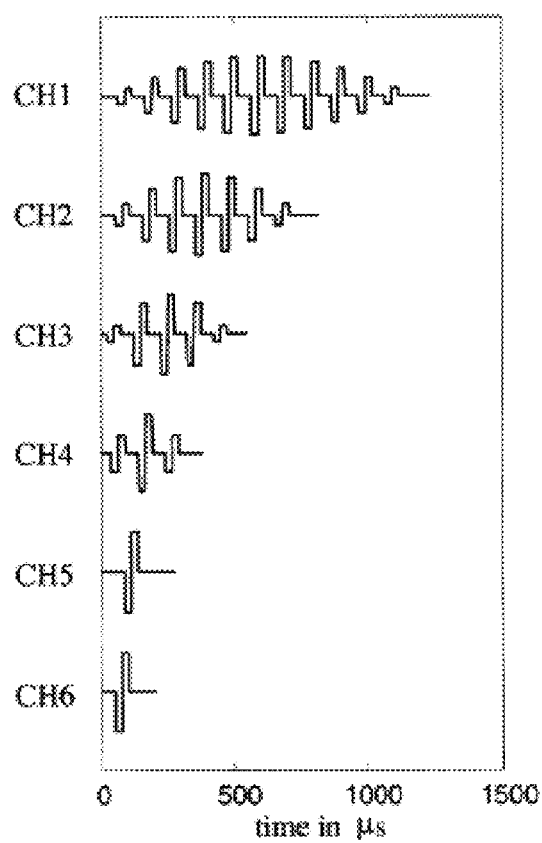
FIGS. 2A and 2B show channel specific sampling sequences (CSSS) for two 6-channel systems utilizing biphasic pulses at 10 kpps and phase duration of 25 μs.
Figure 2B:
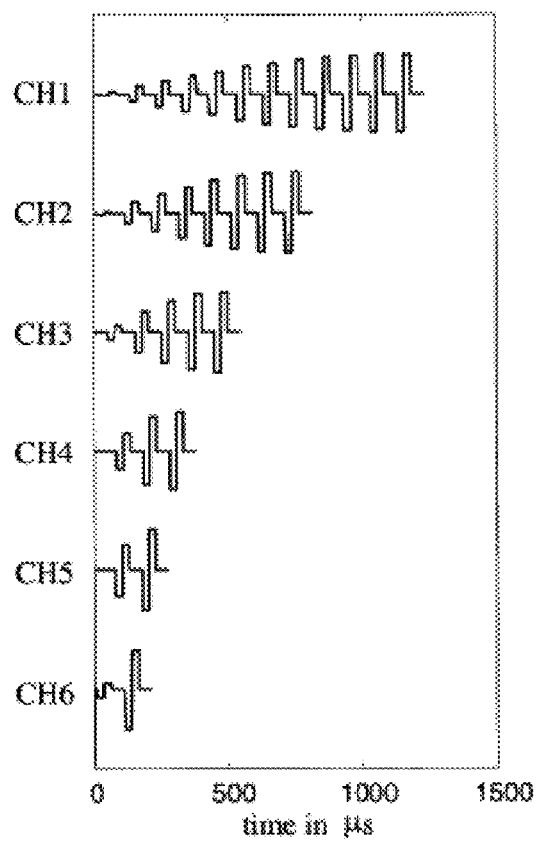
Figure 3:
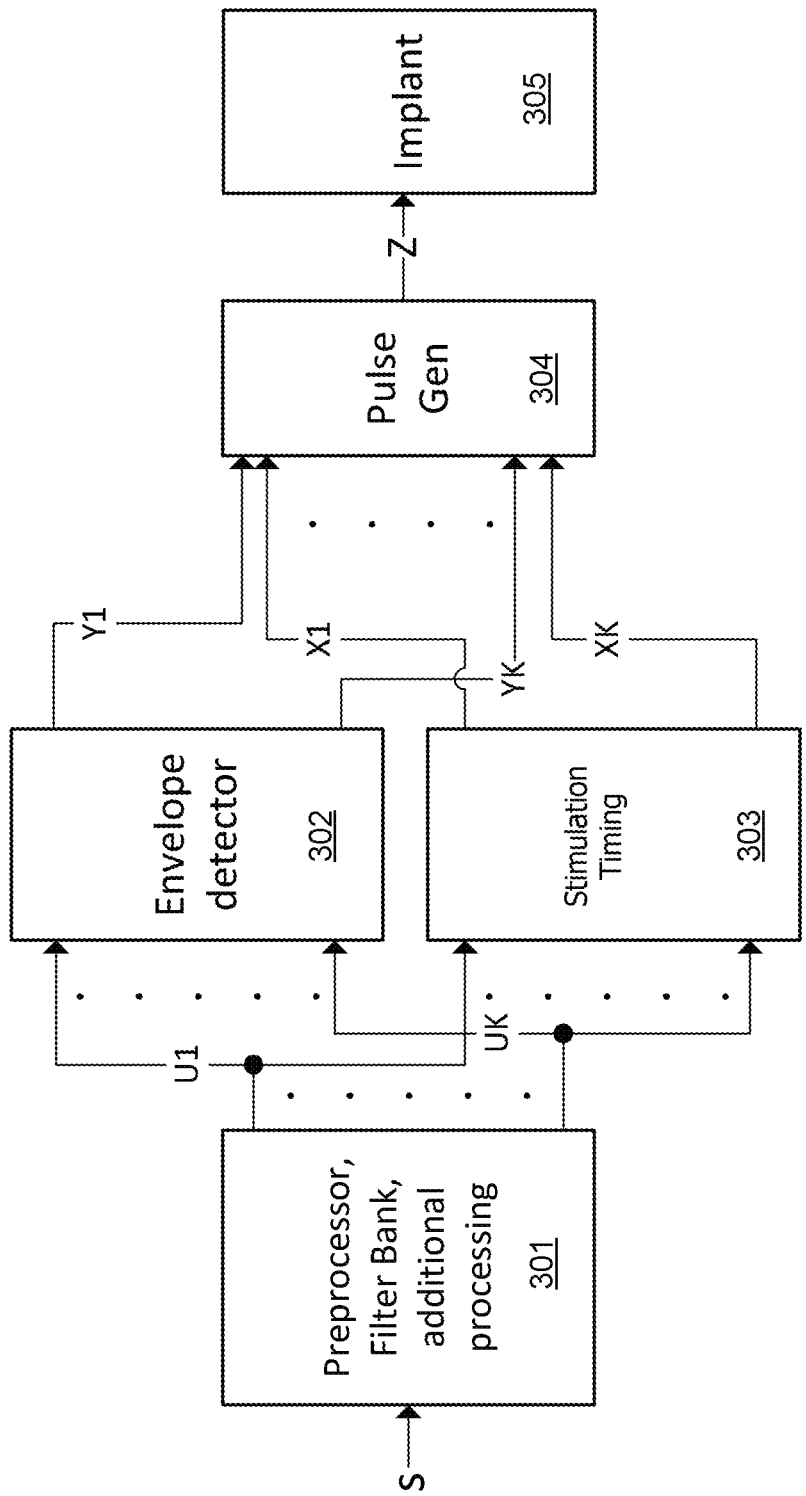
FIG. 3 shows various functional blocks in a signal processing arrangement for a hearing implant according to a prior art arrangement.
Figure 4:
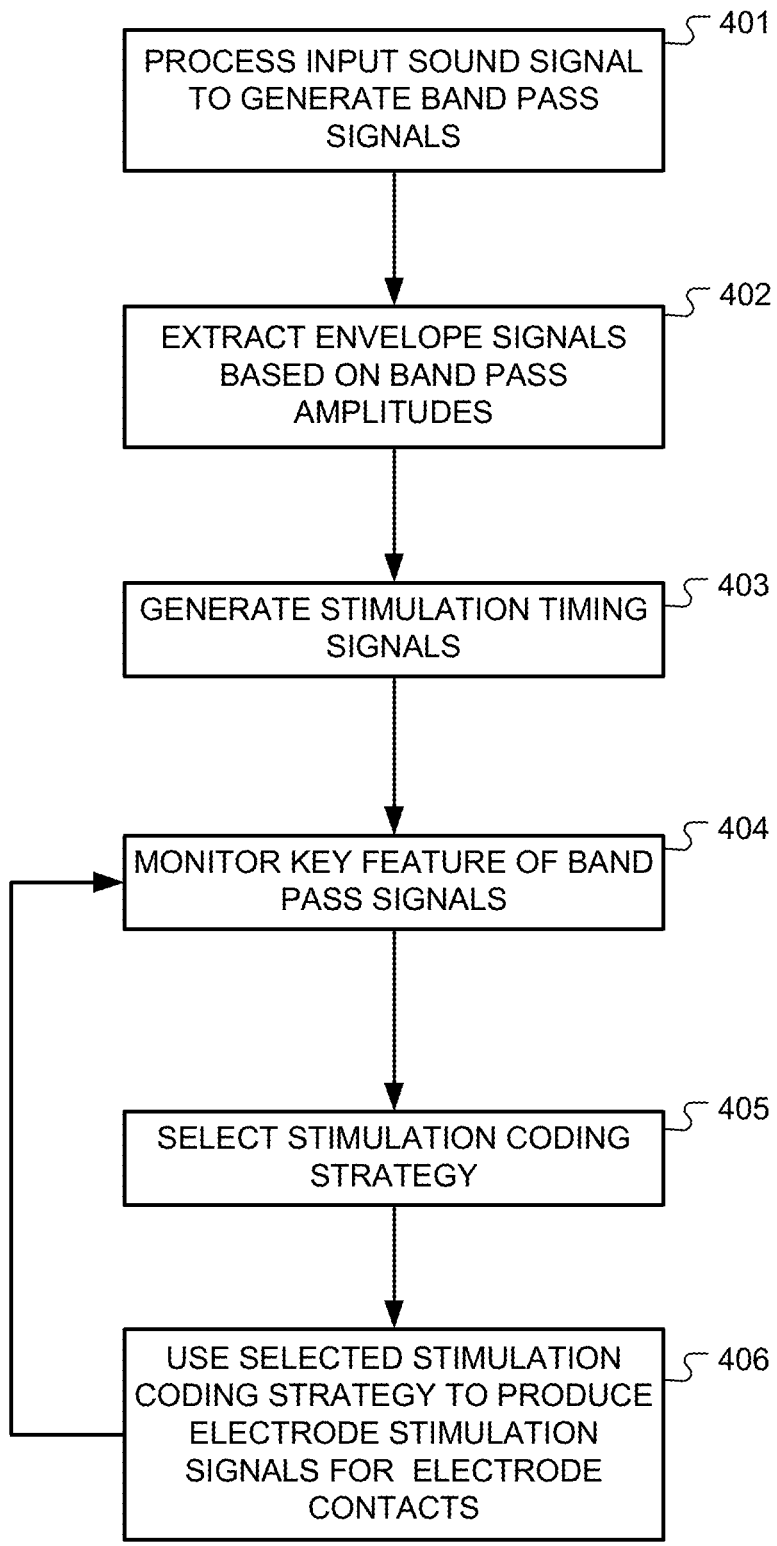
FIG. 4 shows various logical steps in developing electrode stimulation signals according to an embodiment of the present invention.
Figure 5:
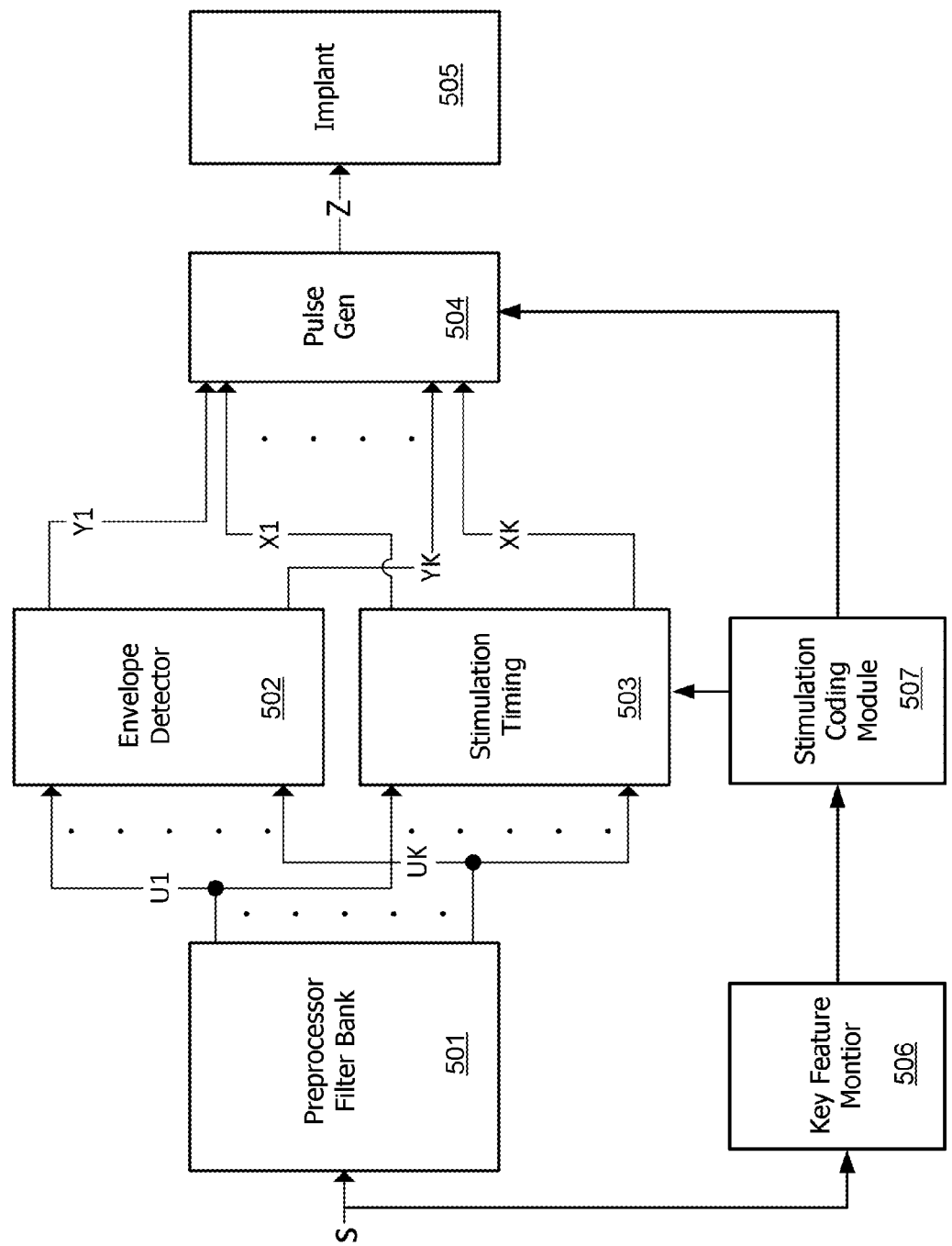
FIG. 5 shows various functional blocks in a signal processing arrangement for a hearing implant according to an embodiment of the present invention.

FIG. 5 shows various functional blocks in a signal processing arrangement for a cochlear implant and FIG. 4 is a flow chart showing various logical steps in producing electrode stimulation signals to electrode contacts in an implanted cochlear implant array according to an embodiment of the present invention. A pseudo code example of such a method can be set forth as:

Input Signal Preprocessing:
    BandPassFilter (input_sound, band_pass_signals)
Envelope Extraction:
    BandPassEnvelope (band_pass_signals, band_pass_envelopes)
Stimulation Timing Generation:
    TimingGenerate (band_pass_signals, stim_timing)
Key Feature Monitor:
    KeyMonitor (band_pass_signals, key_feature)
Stimulation Coding:
    CodingSelect (key_feature, coding_strategy)
Pulse Generation:
    PulseGenerate (band_pass_envelopes, stim_timing, coding_strategy, out_pulses)

The details of such an arrangement are set forth in the following discussion.

In the arrangement shown in FIG. 5, the input sound signal is produced by one or more sensing microphones, which may be omnidirectional and/or directional. Preprocessor Filter Bank 501 pre-processes this input sound signal, step 401, with a bank of multiple parallel band pass filters, each of which is associated with a specific band of audio frequencies; for example, using a filter bank with 12 digital Butterworth band pass filters of 6th order, Infinite Impulse Response (IIR) type, so that the input sound signal is filtered into some K band pass signals, $U_1$ to $U_K$ where each signal corresponds to the band of frequencies for one of the band pass filters. Each output of the Preprocessor Filter Bank 501 can roughly be regarded as a sinusoid at the center frequency of the band pass filter which is modulated by an amplitude envelope signal. This is due to the quality factor ($Q \approx 3$) of the filters. In case of a voiced speech segment, the band pass envelope is approximately periodic, and the repetition rate is equal to the pitch frequency. Alternatively and without limitation, the Preprocessor Filter Bank 501 may be implemented based on use of a fast Fourier transform (FFT) or a short-time Fourier transform (STFT). Based on the tonotopic organization of the cochlea, each electrode contact in the scala tympani typically is associated with a specific band pass channel of the Preprocessor Filter Bank 501. The Preprocessor Filter Bank 501 also may perform other initial signal processing functions such as automatic gain control (AGC) and/or noise reduction.

Figure 6:
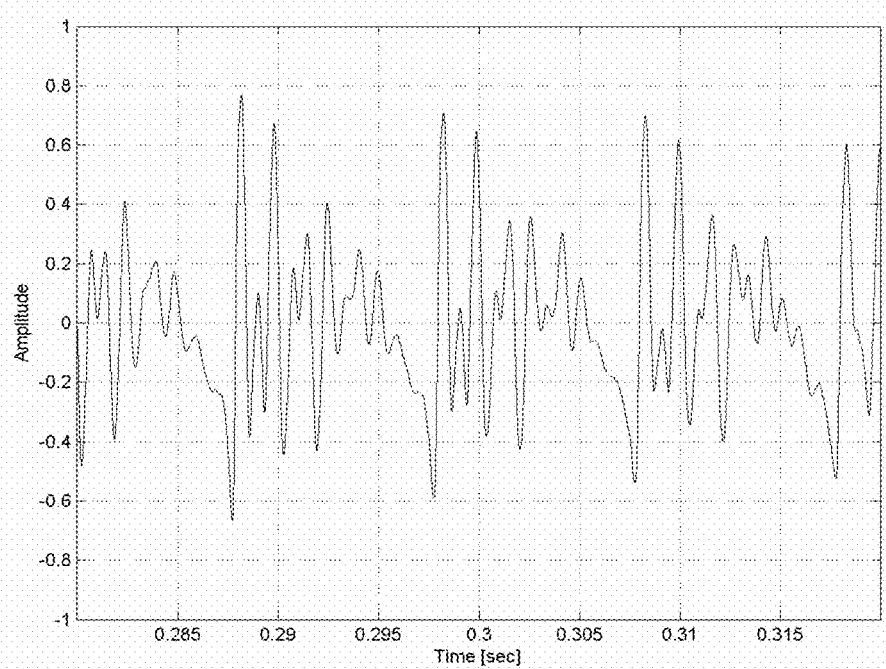
FIG. 6 shows an example of a short time period of an audio speech signal from a microphone.
Figure 7:
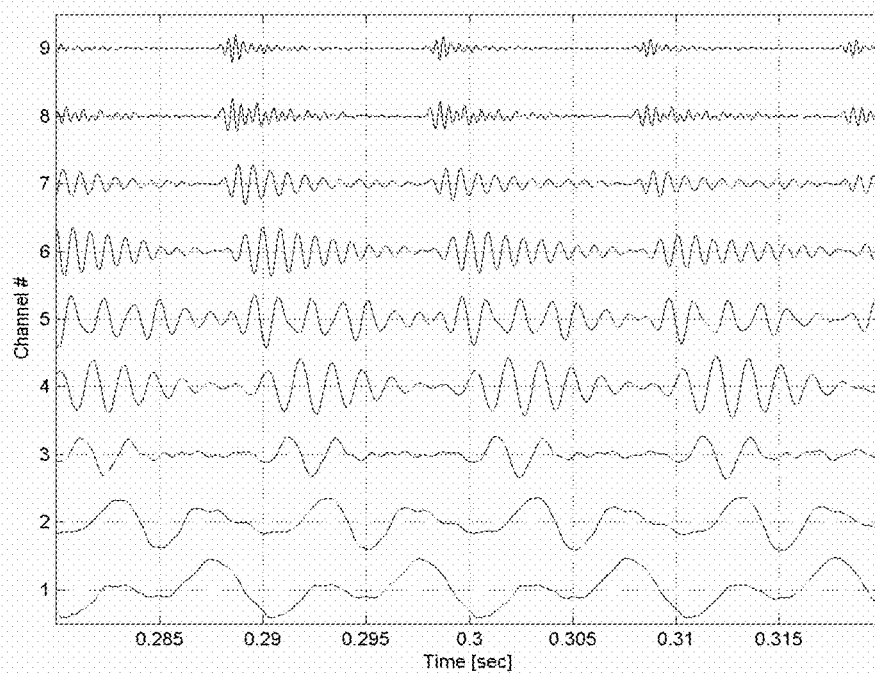
FIG. 7 shows an acoustic microphone signal decomposed by band-pass filtering by a bank of filters into a set of band pass signals.

FIG. 6 shows an example of a short time period of an input speech signal from a sensing microphone, and FIG. 7 shows the microphone signal decomposed by band-pass filtering by a bank of filters. An example of pseudocode for an infinite impulse response (IIR) filter bank based on a direct form II transposed structure is given by Fontaine et al., Brian Hears: *Online Auditory Processing Using Vectorization Over Channels*, Frontiers in Neuroinformatics, 2011; incorporated herein by reference in its entirety:

```
for j = 0 to number of channels − 1 do
    for s = 0 to number of samples − 1 do
        Y_j(s) = B_0j * X_j(s) + Z_0j
        for i = 0 to order − 3 do
            Z_ij = B_{i+1 j} * X_j(s) + Z_{i+1 j} − A_{i+1 j} * Y_j(s)
        end for
        Z_{order − 2,j} = B_{order − 1 j} * X_j(s) − A_{order − 1 j} * Y_j(s)
    end for
end for
```

The band pass signals $U_1$ to $U_K$ (which can also be thought of as electrode channels) are output to an Envelope Detector 502 and a Stimulation Timing Module 503. The Envelope Detector 502 extracts characteristic envelope signals outputs $Y_1, \ldots, Y_K$, step 402, that represent the channel-specific band pass envelopes. The envelope extraction can be represented by $Y_k = LP(|U_k|)$, where |.| denotes the absolute value and LP(.) is a low-pass filter; for example, using 12 rectifiers and 12 digital Butterworth low pass filters of 2nd order, IIR-type. A properly selected low-pass filter can advantageously smooth the extracted envelope to remove undesirable fluctuations. Alternatively, if the band pass signals $U_1, \ldots, U_K$ are generated by orthogonal filters, the Envelope Detector 502 may extract the Hilbert envelope. In some embodiments, the Envelope Detector 502 may also be configured to determine one or more useful features of the band pass envelope such as envelope slope (e.g., based on the first derivative over time of the envelope), envelope peak (ascending slope/positive first derivative followed by descending slope/negative first derivative), and/or envelope amplitude of the band pass envelope.

The Stimulation Timing Module 503 processes selected temporal fine structure features for one or more of the band pass signals $U_1, \ldots, U_K$ (typically, for one or more of the most apical, lowest frequency channels) such as negative-to-positive zero crossings to generate stimulation timing signals $X_1, \ldots, X_K$. In the following discussion, the band pass signals $U_1, \ldots, U_K$ are assumed to be real valued signals, so in the specific case of an analytic orthogonal filter bank, the Stimulation Timing Module 503 considers only the real valued part of $U_k$. For the selected band pass signals, the Stimulation Timing Module 303 generates stimulation timing signals reflecting the temporal fine structure features, step 403. In some embodiments, the Stimulation Timing Module 303 may limit the instantaneous band pass frequency $f_0$ to the upper and lower frequency boundaries $f_{L1}$ and $f_{U1}$ of the respective filter band. For example, a given band pass signal may have a lower frequency boundary $f_{L1}$ of 500 Hz and an upper frequency boundaries of $f_{U1}$=750 Hz.

A Key Feature Monitor 506 monitors one or more key features present in the input sound signal or the band pass signals, step 404. For example, the key feature monitored by the Key Feature Monitor 506 may be the signal to noise ratio (SNR) of the input sound signal, the direct to reverberation ratio (DRR) of the input sound signal.

A Stimulation Coding Module 507 is coupled to the Key Feature Monitor 506 and selects a stimulation coding strategy for one or more selected band pass signals based on the key feature value, step 405. The stimulation coding strategies include: (1) an envelope-based stimulation coding strategy based on the band pass envelope signals (such as CIS or HD-CIS that uses stimulation pulses at a constant stimulation rate), and (2) an event-based stimulation coding strategy that transmits temporal fine structure information based on the stimulation timing signals (such as FSP or FS4 that uses adaptive stimulation rates according to the temporal fine structure information). It is assumed that event-based stimulation coding strategies are optimal in relatively quiet listening conditions, while envelope-based stimulation coding strategies are better in noisier conditions. The Stimulation Coding Module 507 automatically switches between different selected stimulation coding strategies as a function of changes in the key feature value monitored by the Key Feature Monitor 506. The Stimulation Coding Module 507 may be configured to switch between different selected stimulation coding strategies directly without a transition period of time, or it may switch between different selected stimulation coding strategies by adaptively changing the selected stimulation coding strategy over a transition period of time to become a different stimulation coding strategy; for example, either after or while the key feature value changes from an initial value to a coding change value.

A Pulse Generator 504 uses the stimulation coding strategy selected by the Stimulation Coding Module 507 to produce the electrode stimulation signals for the electrode contacts in the Implant 505, step 406. For example, the Pulse Generator 504 may be configured to creates CSSS output timing request pulses at the start of the negative to positive zero crossings of each of one or more selected band pass signals and then weight (amplitude modulates) the CSSS stimulation pulses with the band pass envelopes from the Envelope Detector 502.

The Pulse Generator 504 also will typically further adjust output electrode stimulation signals based on a non-linear mapping that reflects patient-specific scaling from the fitting process. Similarly, variations in perceived loudness in event-based stimulation coding and envelope-based stimulation coding can be handled by adjusting stimulation parameters such as pulse amplitude, pulse duration, pulse shape or shape of the CSSS sequences (e.g. with short interpulse intervals). And again this may be based on patient-specific fitting parameters that are adjusted during presentation of speech signals until speech is perceived most naturally. In addition, the MCL and THR values may vary when switching from one specific stimulation coding strategy to another, so the MCL and THR values of the patient-specific scaling function should also be adjusted (in addition to the CSSS sequence) to promote a loudness-balanced transition between the different stimulation coding strategies.

Some studies in normal hearing subjects (e.g., Dietz, Mathias, et al. "Emphasis of spatial cues in the temporal fine structure during the rising segments of amplitude-modulated sounds." *Proceedings of the National Academy of Sciences* 110.37 (2013): 15151-15156; incorporated herein by reference in its entirety) suggest that the fine structure information may be most effective during the rising slope of the band pass envelope. Thus, some embodiments may use the rising slope of the band pass envelope as the key feature, or some other characteristic of the envelope. If the key feature is envelope peak, then event-based stimulation coding may be applied during an interval defined around or following the peak, the length of which may be related to the length and the amplitude of the peak. A specific such arrangement may further be configured to use event-based stimulation coding reflecting the fine structure information only when the key feature is above some minimum threshold value—when the rising slope of the envelope is great enough. Otherwise, envelope-based stimulation coding may be used. The envelope slope may be averaged or low-pass filtered over recent past values in order to provide smooth values.

Figure 8:
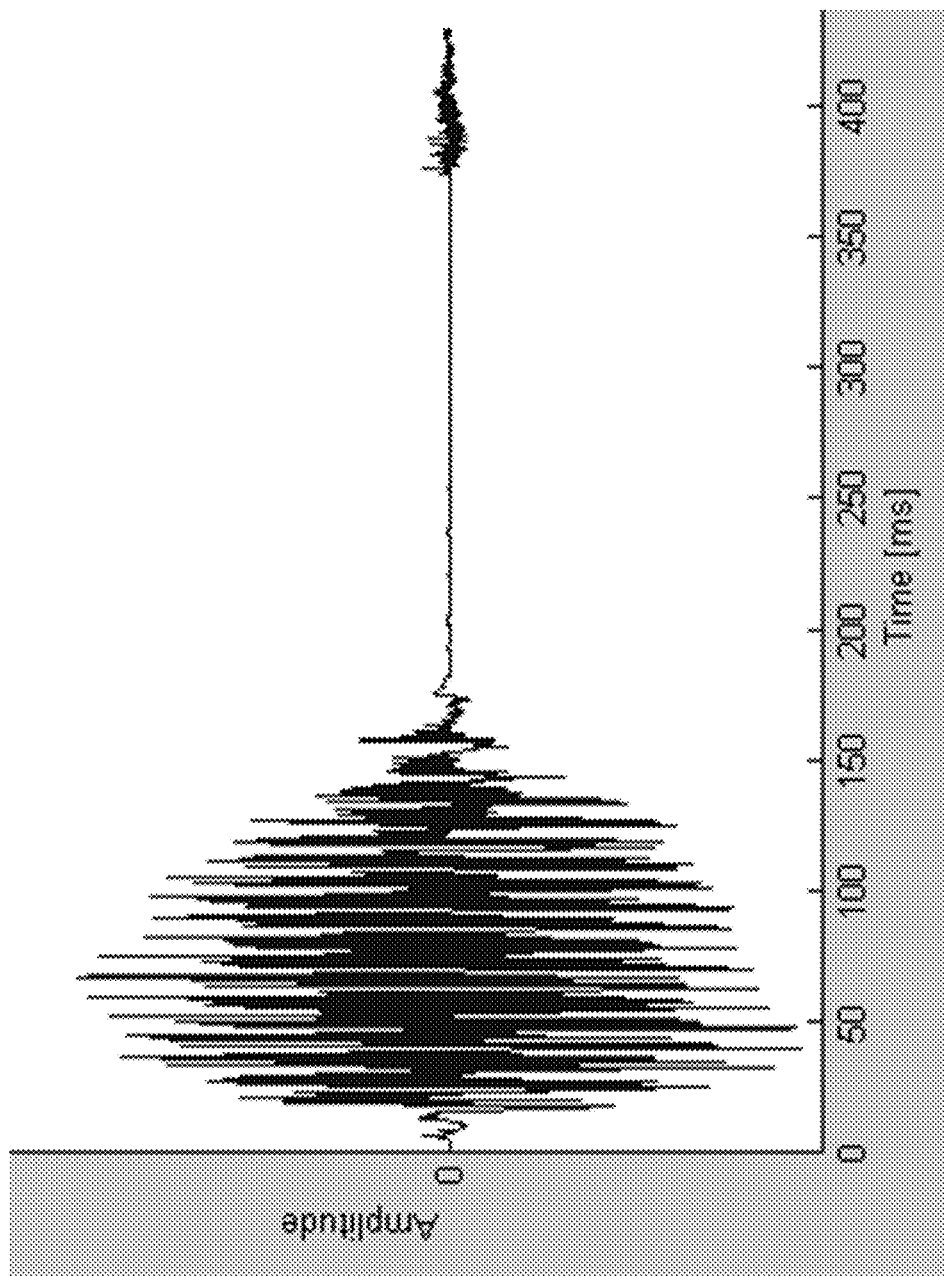
FIG. 8 shows a broadband waveform signal for the syllable "bet".
Figure 9:
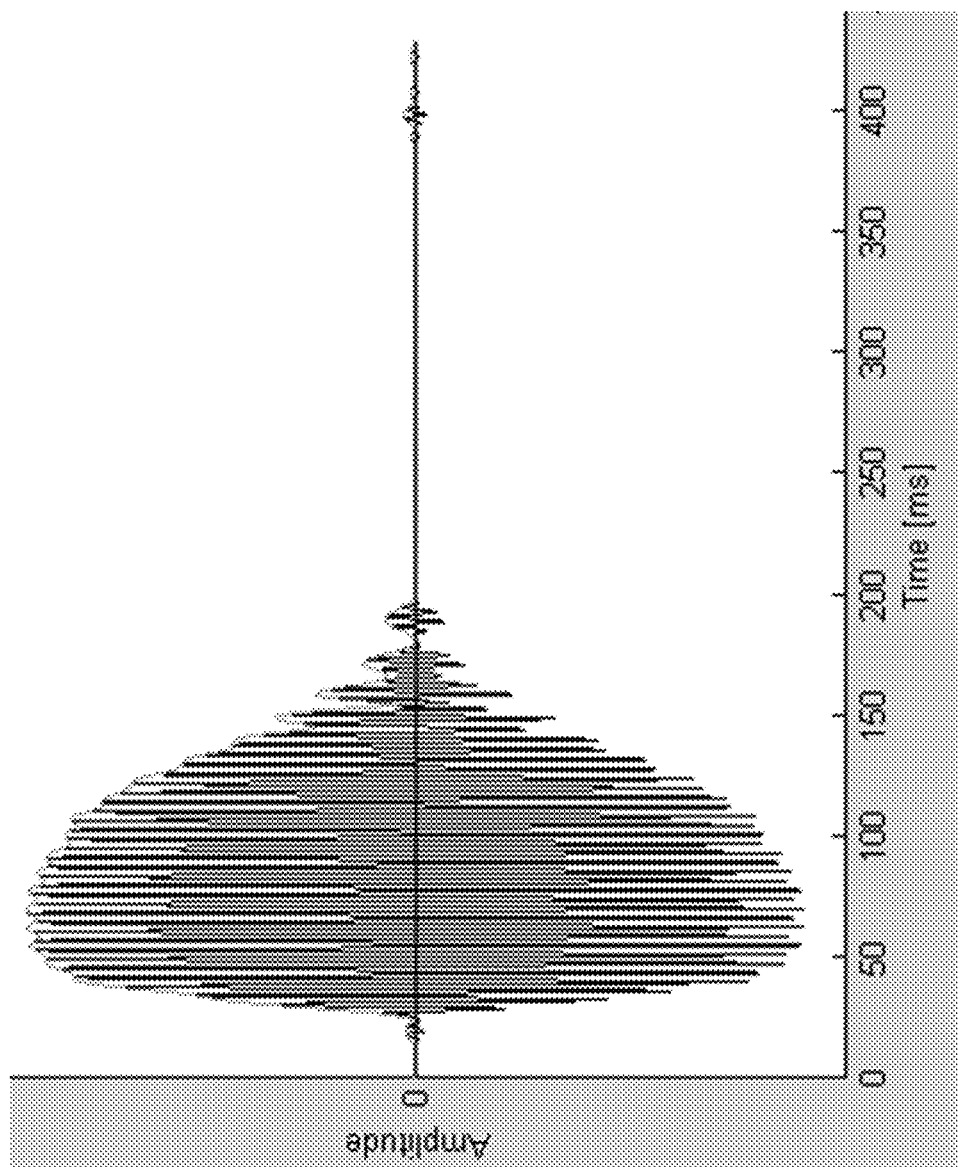
FIG. 9 shows a band pass filtered signal and envelope signal for the waveform of FIG. 8.
Figure 10:
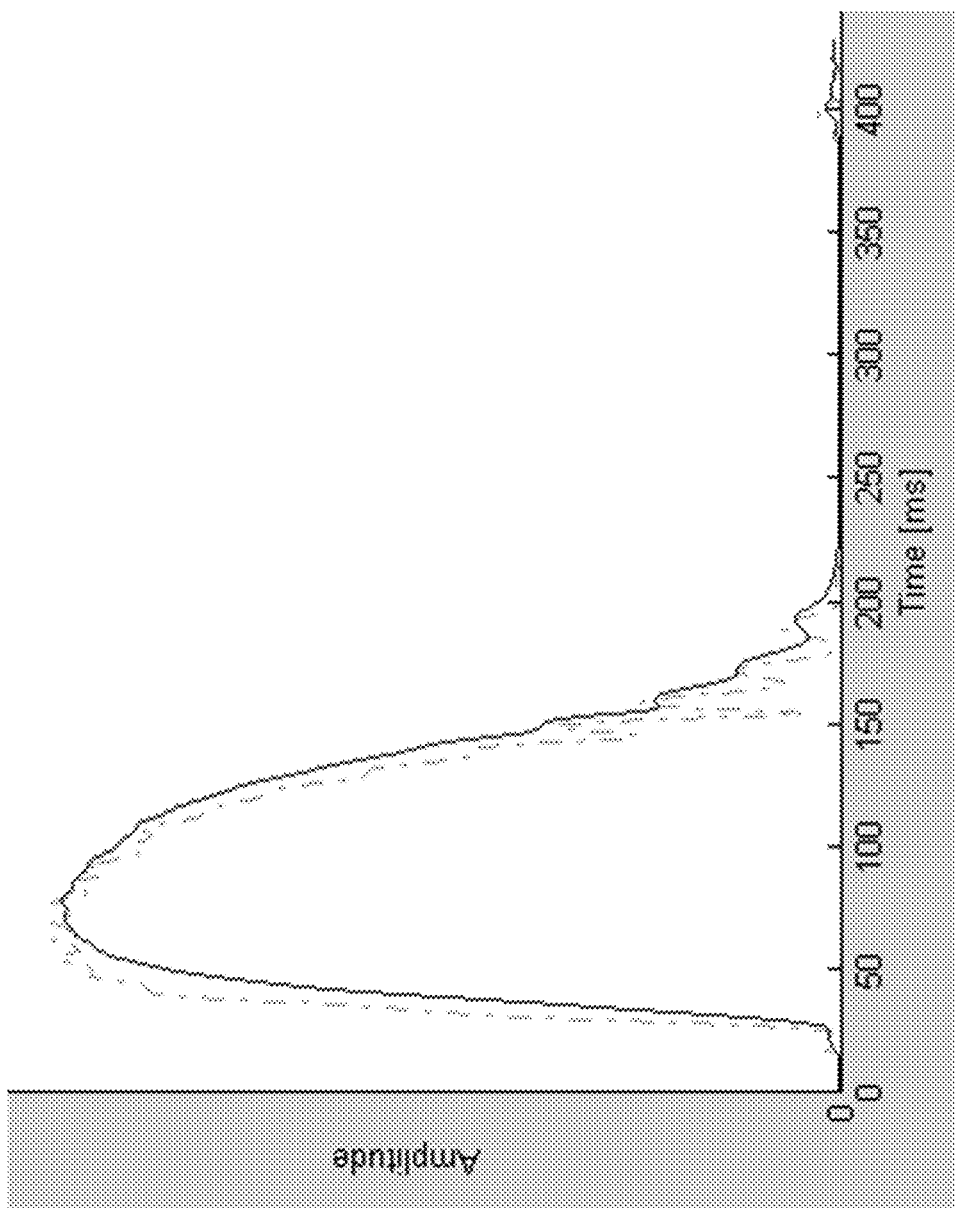
FIG. 10 shows an envelope signal and smoothed envelope signal for the waveform in FIG. 9.
Figure 11:
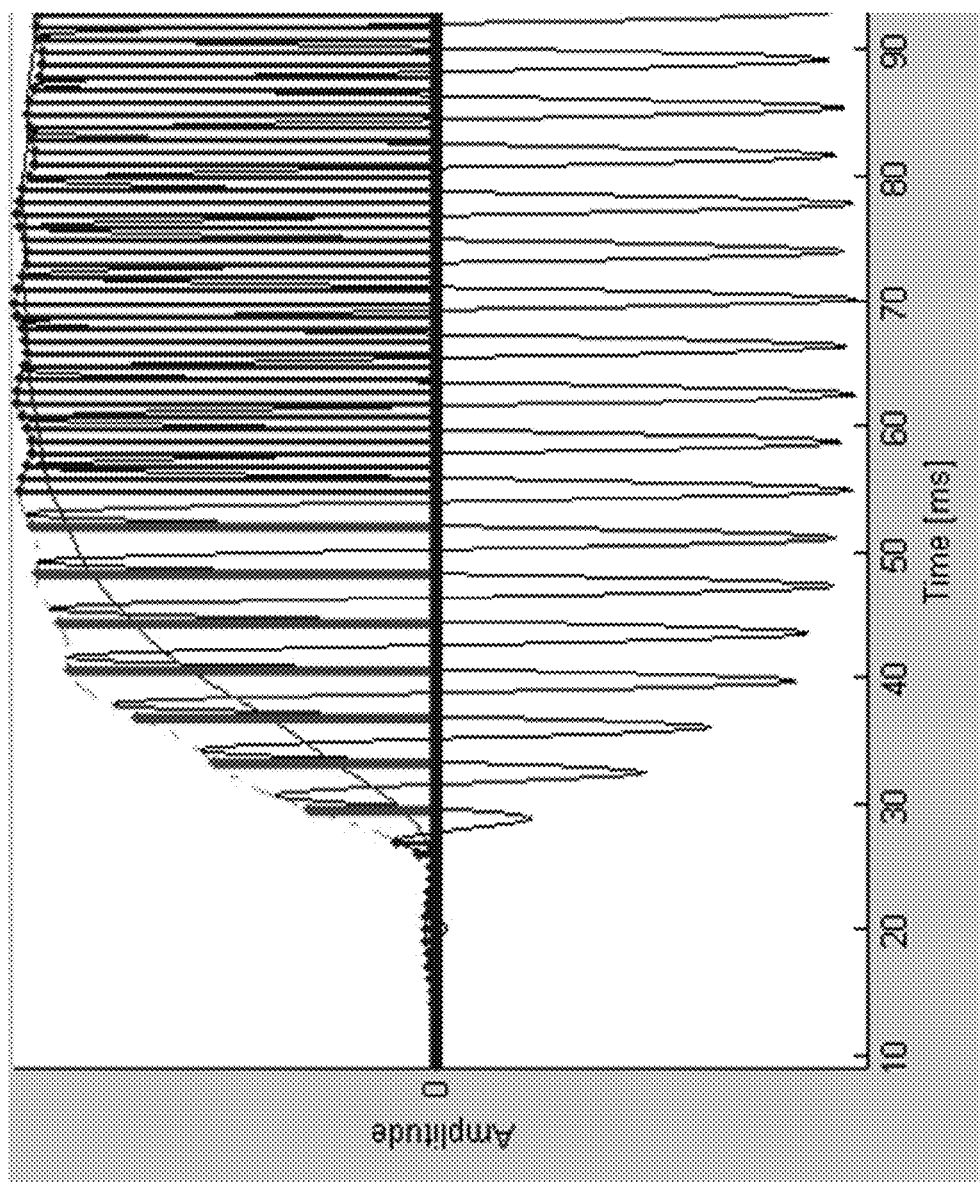
FIG. 11 shows a section of the waveform signal from FIG. 9 with rising slope of the envelope.
Figure 12:
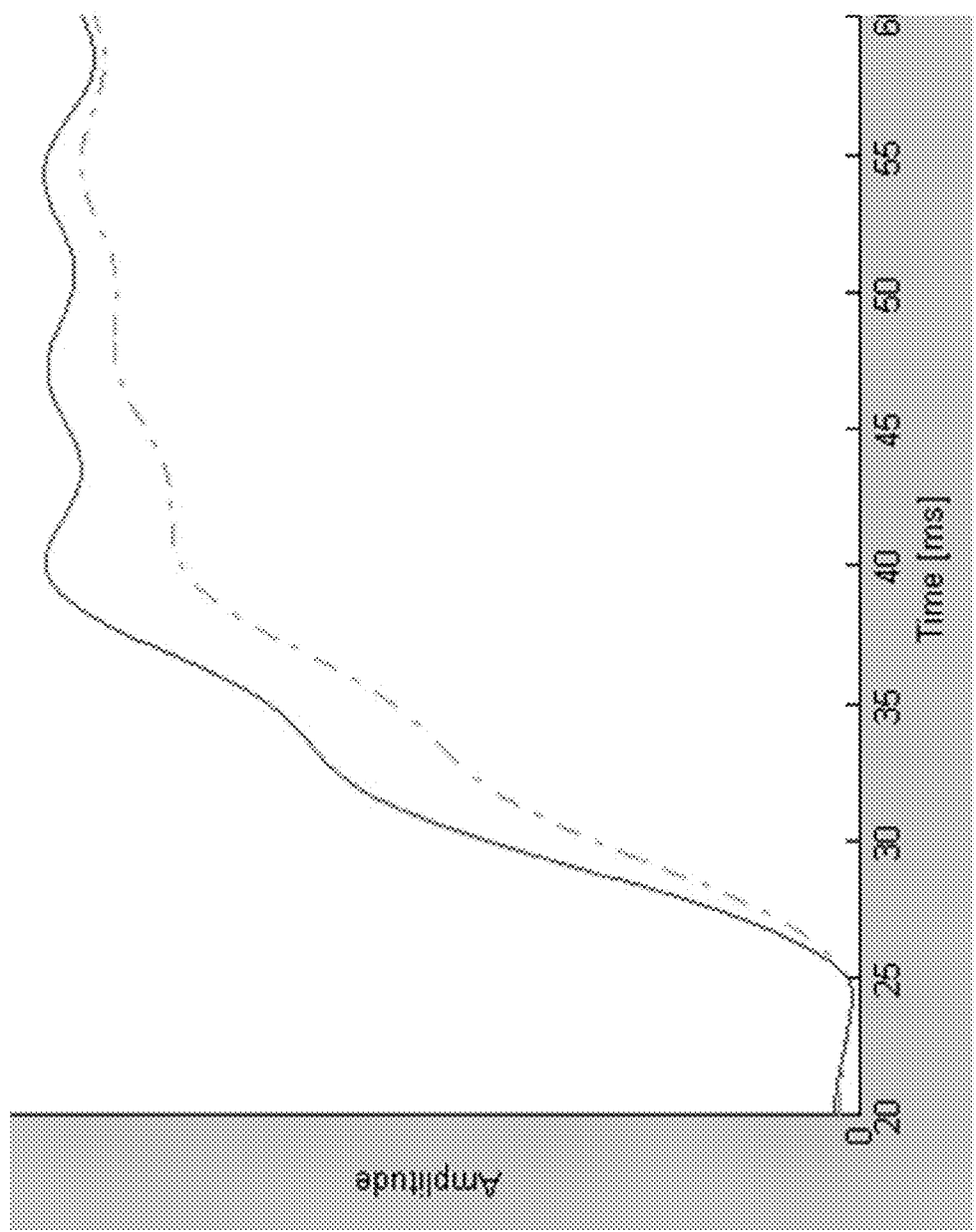
FIG. 12 shows a section of the envelope signal and raised envelope signal from FIG. 11.

For example, FIG. 8 shows a broadband waveform signal for the syllable "bet". FIG. 9 shows a band-pass filtered version of this signal with a lower frequency boundary of 200 Hz and an upper frequency boundary of 325 Hz together with the band-pass envelope. FIG. 10 shows the band-pass envelope and a smoothed version of this envelope derived by low-pass filtering with 100 Hz. In FIGS. 11 and 12, the stimulation pulses are controlled by this smoothed envelope: if the slope of the envelope exceeds a certain threshold (here 0.001), then fine structure stimulation is applied using single pulses at zero-crossings of the band-pass signal. These pulses at zero-crossings are weighted with the corresponding band-pass envelope. At times where the envelope slope does not exceed the minimum threshold, envelope-only stimulation may be applied using a regular time-grid for stimulation pulses where the pulses are weighted with the corresponding envelope signal.

As stated above, in some specific embodiments, the Stimulation Coding Module 507 may be configured to automatically make a smooth transition between different stimulation coding strategies over a transition period of time based on the SNR of the input sound signal by adaptively modifying the length and the shape of the stimulation timing signals (e.g., channel-specific sampling sequences (CSSS)). For each stimulation timing signal from the Stimulation Timing Module 503, the Stimulation Coding Module 507 determines an event-specific length for the CSSS pulse sequence ("FL interval"). The Pulse Generator 504 shapes the CSSS pulse sequence to follow the amplitude of the band pass envelope from the Envelope Detector 502, in effect, sampling the band pass envelope with the CSSS sequence.

When the SNR signal from the Key Feature Monitor 506 is relatively high (quiet sound environment), the Stimulation Coding Module 507 adjusts the FL interval to be so short that a CSSS pulse sequence may consist of as little as a single pulse. As the SNR signal from the Key Feature Monitor 506 decreases (the environment becomes noisier), the Stimulation Coding Module 507 increases the FL interval and adds more pulses to the CSSS sequence until at some point for a low SNR (high noise), the last pulse of the CSSS sequence is seamlessly followed by the first pulse of the next CSSS sequence, resulting in a continuous (constant rate) sampling of the band pass envelopes from the Envelope Detector 502. If the length of the FL interval becomes larger than the time between two consecutive trigger events (i.e., two zero crossings), the Stimulation Coding Module 507 may terminate the existing CSSS sequence when the next trigger event occurs and the FL interval of the following trigger event overrules the previous FL interval. Or the Stimulation Coding Module 507 may continue with the CSSS pulse sequence initiated by the first trigger event and ignore the subsequent trigger event so that the end of the existing FL interval, a new FL interval is determined. Once the SNR signal from the Key Feature Monitor 506 increases again, the Stimulation Coding Module 507 adaptively adjusts the FS interval to again become shorter than the times between the trigger events.

Figure 13:
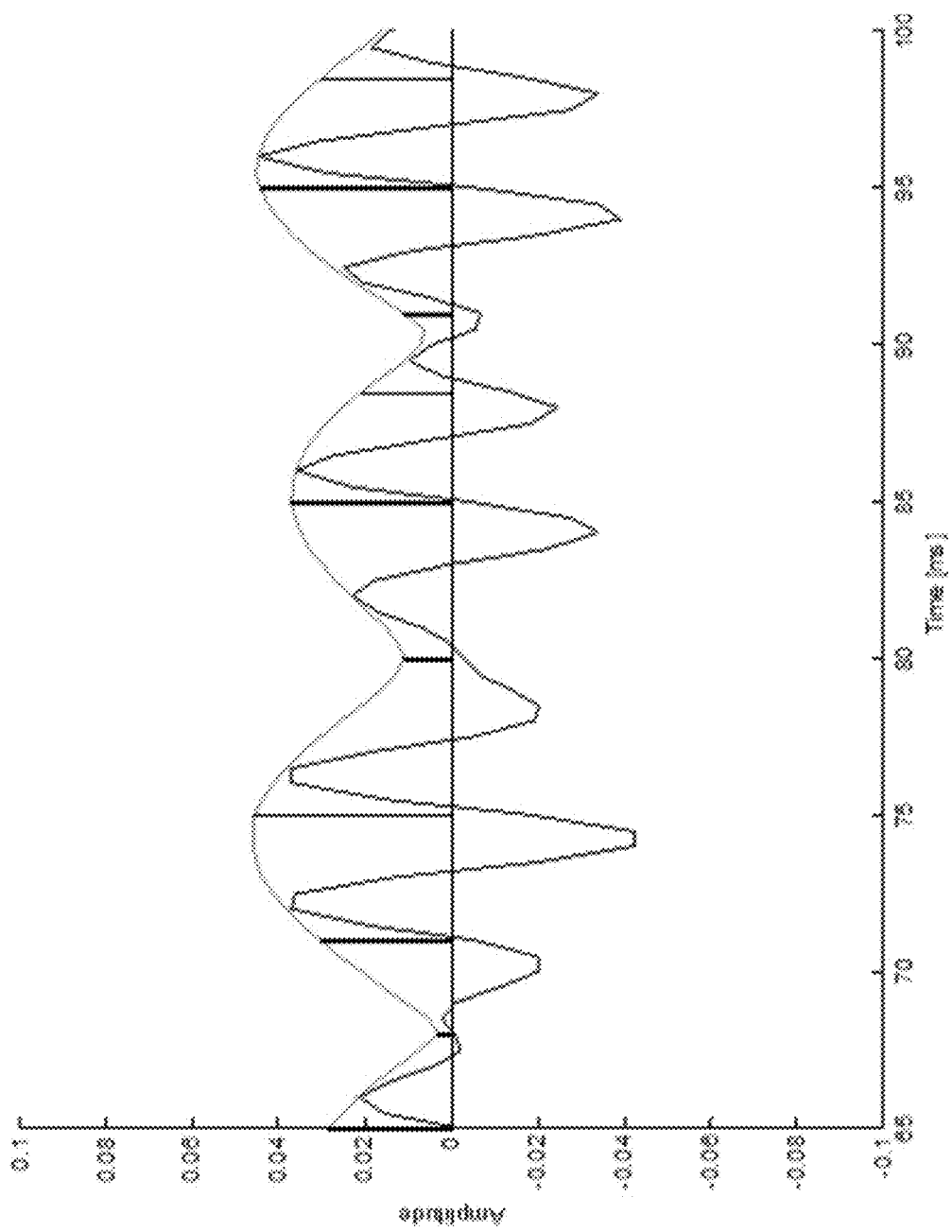
FIG. 13 shows an example of a processed band pass signal and the resulting CSSS pulse sequence for a vowel with added Gaussian noise and a SNR=10 dB.
Figure 14:
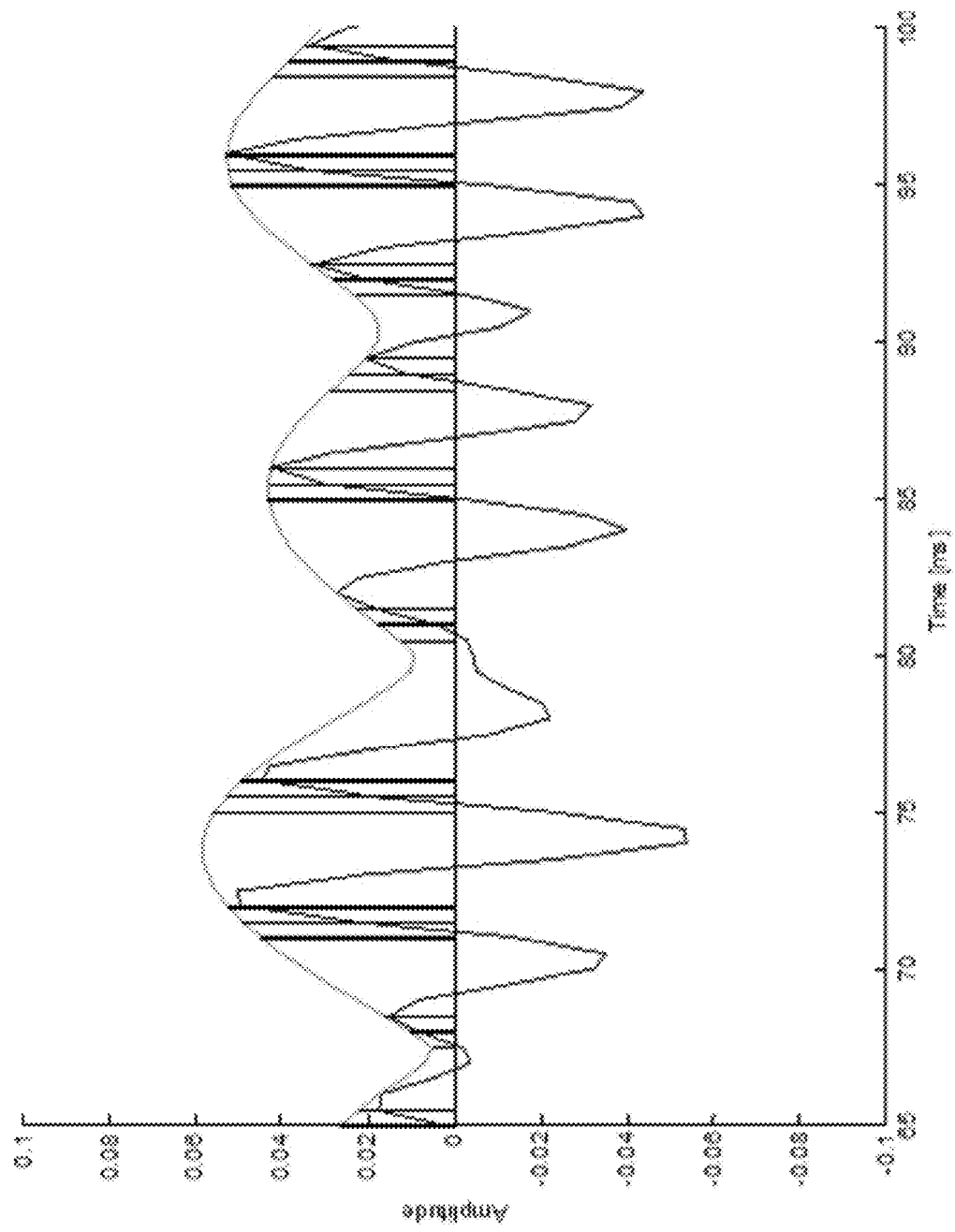
FIG. 14 shows the same signal as in FIG. 13, with SNR=5 dB.
Figure 15:
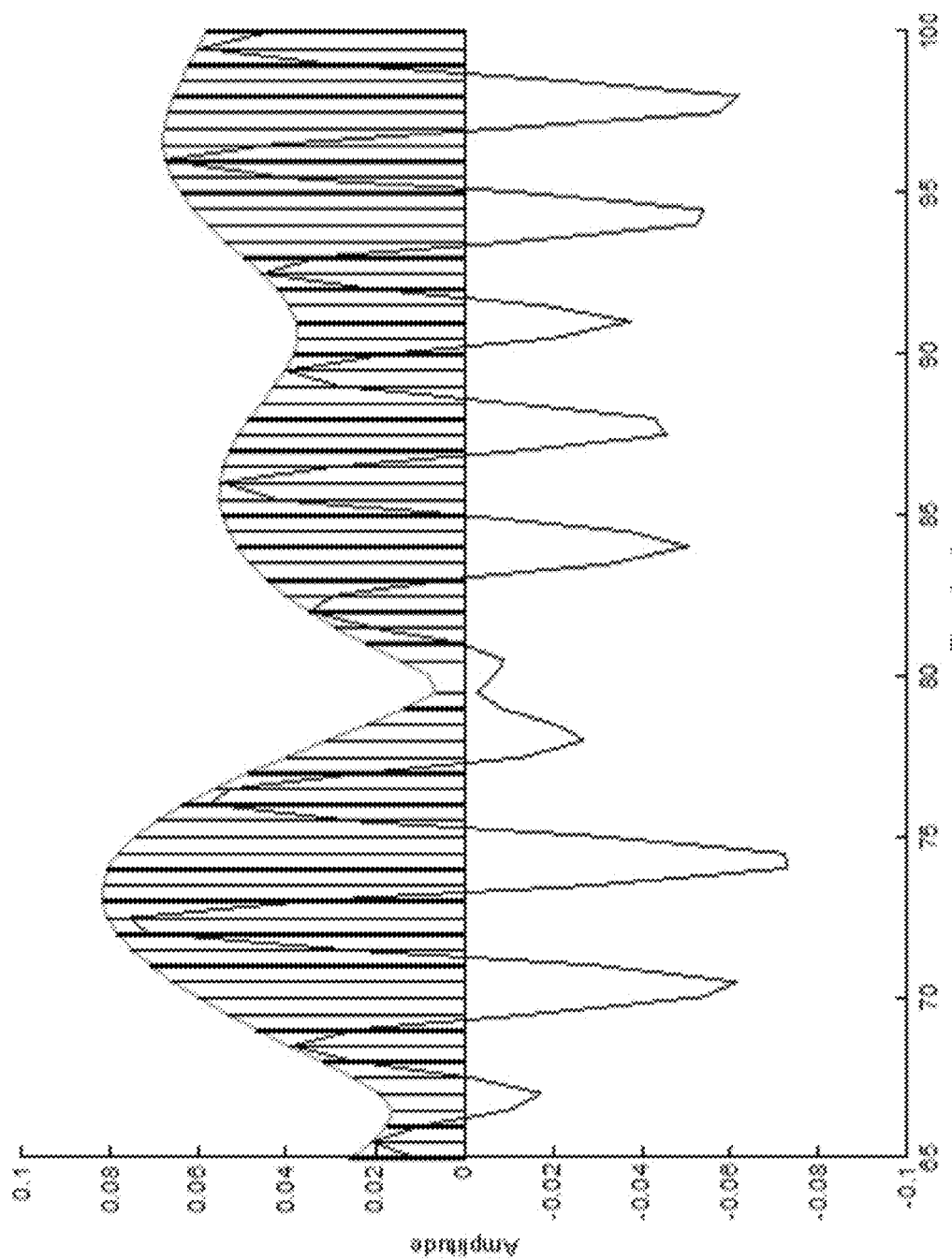
FIG. 15 shows the same signal as in FIG. 13, with SNR=0 dB.

FIG. 13 shows an example of a processed band pass signal and the resulting CSSS pulse sequence for a vowel with added Gaussian noise and a SNR=10 dB. The band pass signal is the higher frequency full sine wave signal in green, the Hilbert band pass envelope is the slower varying half sine wave trace shown in blue, and the vertical black lines represent the applied CSSS sequences with a sequence length of one. FIG. 14 shows the same signal as in FIG. 13, when the SNR signal decreases down to 5 dB (more noise) and the FL interval is increased so that the CSSS sequences contain three pulses each. FIG. 15 shows the same signal as in FIG. 13, with SNR=0 dB (noisier still) where the FL interval is so long that the CSSS sequence performs a continuous sampling of the band pass envelope that is similar to the HD-CIS coding strategy.

In some embodiments, the Stimulation Coding Module 507 may be configured to switch between different selected stimulation coding strategies as a function of changes in the key feature value monitored by the Key Feature Monitor 506 and further as a function of more features of the band pass envelope from the Envelope Detector 502; for example, the envelope amplitude, envelope slope and/or envelope peak value. Thus, where the key feature value is SNR, for high SNR, the Stimulation Coding Module 507 may trigger a CSSS sequence at each zero-crossing of the band pass signal, while for lower SNR values, the Stimulation Coding Module 507 may trigger a CSSS sequence only for zero crossings with a certain threshold minimum envelope value (e.g., from the Hilbert envelope). This envelope threshold functionality may be advantageous in noisy environments (low SNR) to better distinguish between zero crossing events just caused by noise and those actually caused by a speech or musical signal. The threshold minimum envelope may be channel-specific in some embodiments, while in other embodiments, it is not. Of course, some other key feature may be used, for example, direct to reverberation ratio (DRR).

In addition to or alternatively to adaptively varying the length of the CSSS interval, other specific embodiments may adaptively control other signal variables. For example, in combination with the application of a CSSS pulse at a specific event (e.g. a zero crossing event), a subsequent time interval—fine structure FS-interval—may be determined within which a pulse has to be applied. The length of this FS-interval may be determined by the value of the SNR signal at the time when the pulse has been applied: If the SNR is high, the FS-interval may be chosen to be long, while if the SNR is low, the FS-interval may be chosen to be short. To restrict the stimulation rate to a maximum value that reflects the refractory period of the auditory nerve fibers, a shortest possible FS-interval can be defined that corresponds to the maximum stimulation rate. There are several different specific possibilities:

If another timing event occurs within the FS-interval determined from the previous timing event, and the time between the two timing events is greater than the refractory period, then a pulse can be applied at the second timing event and a new FS-interval is initiated that overrules the previous one.

If another timing event occurs within the FS-interval determined from the previous timing event, but the time between the two timing events is shorter than the refractory period, then a pulse can be applied at the end of the refractory period and a new FS-interval is initiated that overrules the previous one.

If no additional timing event appears before the end of the current FS-interval and the refractory period is shorter than the FS-interval, then another pulse can be applied (forced) at the end of the FS-interval.

If no additional timing event appears before the end of the current FS-interval interval, but the refractory period is greater than the FS-interval, then another pulse can be applied (forced) at the end of the refractory period.

In general, an embodiment may require that a subsequent pulse (either caused by the occurrence of a timing event or by the end of the FS-interval) can only be applied if a minimum period (e.g. the refractory period) is over. In some applications, it may be advantageous to have a shorter period than the refractory period as the minimum period.

Figure 16:
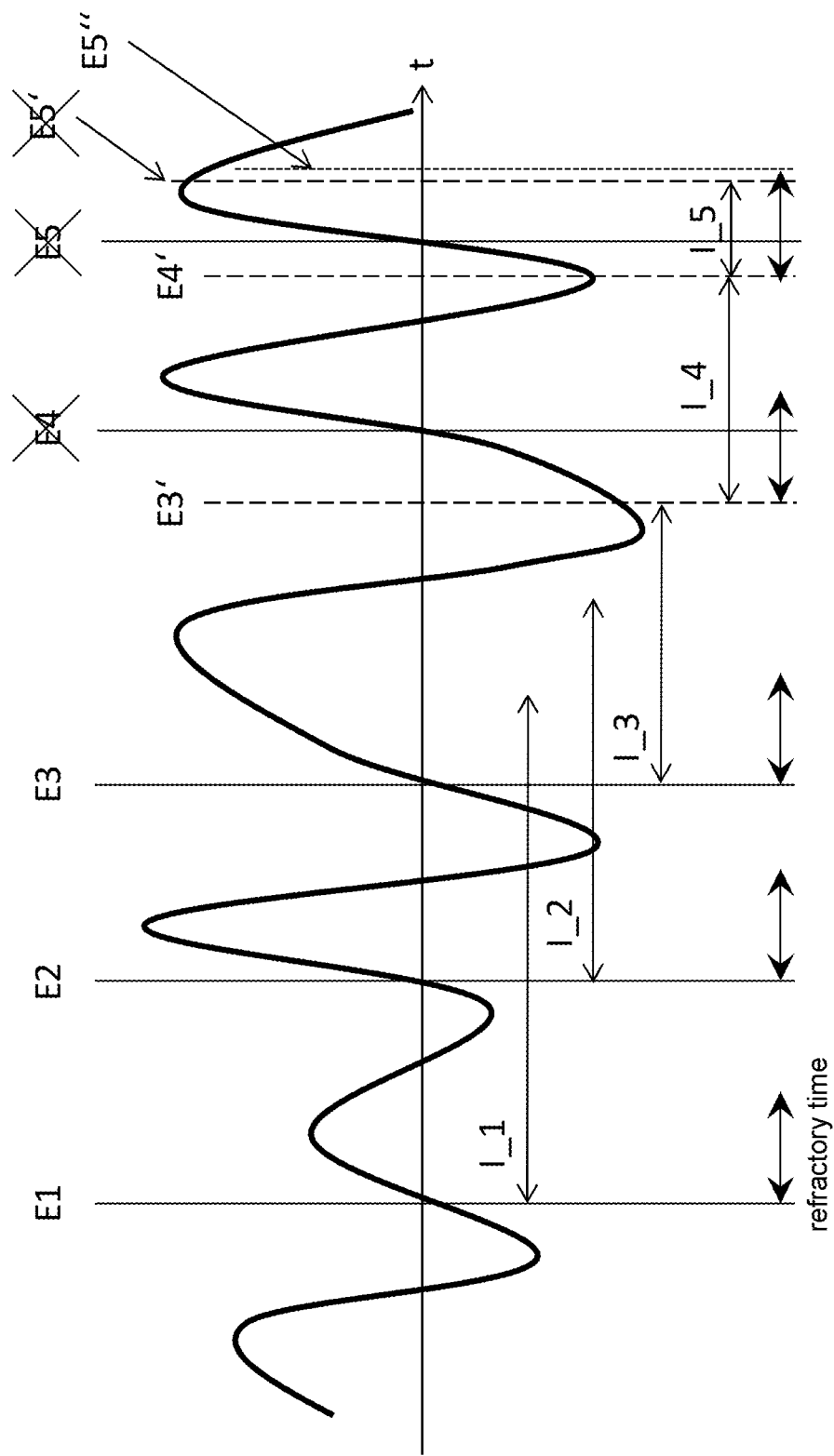
FIG. 16 shows an example of a processed band pass signal and SNR-adapted pulse time intervals according to an embodiment of the present invention.

FIG. 16 shows an example of a processed band pass signal and SNR-adapted pulse time intervals according to an embodiment of the present invention. In FIG. 9, it is assumed that five zero crossing timing events E1-E5 (vertical solid lines) are detected, the SNR is decreasing over time t (i.e. from left to right), and the refractory period is as shown by the corresponding horizontal arrows across the bottom the figure denoted as "refractory time". The first CSSS pulse is, without limitation, applied at the zero crossing event E1. Since the SNR is high, the corresponding FS-interval I_1 is relatively long. The next zero crossing event E2 occurs before the end of the I_1 FS-interval, so the next CSSS pulse is applied at E2, and the same situation with I_2 and E3 although the SNR has meantime decreased so that I_2 is shorter than I_1. However, at the event E3' that occurs at the end of the I_3 FS-interval, a CSSS pulse is forced because no further zero crossing has occurred within this FS-interval starting after zero crossing event E3 (also the refractory time (after E3) is still shorter than I_3). The next zero crossing event occurs at E4, but that is still within the refractory period after the last applied pulse at E3' so there is no pulse applied at E4 nor is any corresponding FS-interval determined. Similarly, at E5 no pulse is applied, and in addition, at E4' the SNR is so low that the corresponding I_5 FS-interval is determined to be shorter than the refractory period so at E5', no pulse is applied but instead is delayed until E5" corresponding to the end of the refractory period after event E4'.

When the SNR later increases more and more (not shown in FIG. 16) the FS-intervals will again become longer and longer until a zero crossing event will be detected after the end of the refractory time but before the end of an FS-interval. From that point on, the zero crossing events will again determine the pulse sequence and the coding strategy follows the known event-based coding strategies until the SNR decreases again. The maximum stimulation rate can be set to be proportional to the inverse of the minimum possible interval (e.g. the refractory period) so that the instantaneous stimulation rate (which equals 1/FS-interval) cannot exceed a given defined value; e.g. a typical rate as presently used for CIS or HD-CIS coding strategies. In general, the lower the SNR, the more the resulting sound coding sequence will be according to an envelope-based coding strategy such as CIS or HD-CIS (constant sampling of each channel in a prescribed manner with the defined maximum stimulation rate). The higher the SNR, the more the resulting sound coding sequence will be like according to a pure event-based coding strategy such as FSP.

The modification of the CSSS sequences can also be done channel-wise, i.e. based on channel-specific SNR values. And while the foregoing was described with SNR being the parameter for subsequent adaptive modifications, other specific signal parameters that characterize the quality of an existing hearing situation may be used as well; e.g. the direct to reverberation ratio (DRR).

Both approaches—variation of CSSS lengths and determination of time intervals within which no pulse is applied—yield similar overall results: a smooth transition between event-based (variable rate) and envelope-based (constant rate) coding strategies. Embodiments of the present invention adapt the sound coding strategy to changes in the sound environment with optimal settings for each environment. With SNR-adjusted sampling, temporal fine structure is provided in situations where it is not disturbed, while the sound coding is morphed seamlessly to a more noise-robust envelope coding for better sound perception in noisier environments.

The foregoing discussion is presented in terms of switching the stimulation coding strategy on one or more band pass channels independently of the stimulation coding strategies used on any other band pass channel. But embodiments of the invention include multi-channel variants which determine key features for multiple band pass channels and coordinate switching their stimulation coding strategies together.

The band pass channels selected for coding temporal fine structure are analyzed with respect to the selected key feature to identify the dominant key features in all the analyzed channels. In n-of-m stimulation coding arrangements, the band pass channels are typically divided into simultaneous time frames and the channel with largest envelope amplitudes in each time frame typically are selected for stimulation. Or envelope slope may serve as the key feature where the dominant channel(s) are those with the largest slope(s). Or the key feature may be envelope peaks where the dominant key features may be the peaks with the largest difference between their amplitudes to the surrounding intra-channel noise level and/or with the smallest full-widths-half-maximum (or a similar measure to characterize the width of the peak). Similarly, if SNR or direct or reverberation ratio (DRR) are the key features, then the band pass channels with the largest values will be considered to be the dominant channels.

For example, in a multi-channel arrangement where envelope slope is used for the key feature, to enhance the transmission of temporal fine structure, only event-based channels (typically the most apical, lowest frequency channels) would be analyzed for the envelope slope, the first derivative in time of the envelope. The non-event-based channels can be stimulated in a regular CIS-type fashion without n-of-m selection. Only event-based channels with a positive first derivative in time of their band-pass envelope would be selected, and from these channels, a subset of band pass channels with the largest envelope amplitude could be chosen for stimulation.

Assume a stimulation frame could comprise sequential ordered fine structure and envelope channels: CH1, CH2, CH3, CH4, CH5, CH6, where channels CH1, CH2 and CH3 are event-based fine structure channels and CH4, CH5 and CH6 are envelope-based channels. For the corresponding slopes of the envelopes SL1, SL2 and SL3, if SL2>0 and SL2>SL1 and SL2>SL3, then SL2 is the dominant key feature and the resulting stimulation frame with one selected event-based channel is CH2, CH4, CH5, CH6. If all the envelope slopes are negative for the event-based channels (no dominant key feature), then no event-based channel is selected and the resulting frame consists only of the envelope-based channels: CH4, CH5, CH6. With two selected event-based channels and SL2>0 and SL1>0 and SL2>SL3 and SL1>SL3, then SL1 and SL2 are the dominant key features and the resulting stimulation frame is: CH1, CH2, CH4, CH5, CH6. In all these examples, on the selected event-based channel(s), the stimulation signal is then developed and applied as described above.

A multi-channel arrangement which determines key features for multiple band pass channels and coordinates switching their stimulation coding strategies is not necessarily specific to an n-of-m strategy. Instead, a single dominant key feature can be selected and event-based stimulation coding can be applied on that channel and its neighbouring channels (provided they are event-based coding channels). So if envelope slope is the key feature, then the channel with a maximum envelope slope is stimulated as described above, together in parallel with the adjacent neighbouring channels. The amplitudes of each of these corresponding stimulation pulses can be derived from the respective band pass envelope signals similar to the CFS-based coding strategy described in U.S. Patent Publication 2009/0254150 (which is incorporated herein by reference in its entirety).

Embodiments of the invention may be implemented in part in any conventional computer programming language such as VHDL, SystemC, Verilog, ASM, etc. Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A computer based method implemented using at least one hardware implemented processor for generating electrode stimulation signals to electrode contacts in an implanted cochlear implant electrode array, the method comprising:

using the at least one hardware implemented processor to perform the steps of:
processing an input sound signal to generate a plurality of band pass signals, wherein each band pass signal represents a band pass channel defined by an associated range of audio frequencies, and wherein each band pass signal has a characteristic amplitude and temporal fine structure features;
extracting band pass envelope signals reflecting time varying amplitude of the band pass signals;
generating stimulation timing signals reflecting the temporal fine structure features of the band pass signals;
monitoring a key feature value present in the input sound signal or the band pass signals;
selecting from the plurality of band pass signals a subset of one or more selected band pass signals;
for the one or more selected band pass signals and for a plurality of stimulation coding strategies, selecting a stimulation coding strategy based on the key feature value, wherein the plurality of stimulation coding strategies include:
  i. an envelope-based stimulation coding strategy based on the band pass envelope signals, and
  ii. an event-based stimulation coding strategy based on the stimulation timing signals;
using the selected stimulation coding strategy to produce the electrode stimulation signals;
delivering the electrode stimulation signals to the electrode contacts in the implanted cochlear implant electrode array; and
switching between different selected stimulation coding strategies as a function of changes in the key feature value.

2. The method according to claim 1, wherein switching between different selected stimulation coding strategies occurs directly without a transition period of time.

3. The method according to claim 1, wherein switching between different selected stimulation coding strategies includes adaptively changing the selected stimulation coding strategy over a transition period of time to become a different stimulation coding strategy.

4. The method according to claim 3, wherein the adaptively changing occurs after the key feature value changes from an initial value to a coding change value.

5. The method according to claim 3, wherein the adaptively changing occurs while the key feature value changes from an initial value to a coding change value.

6. The method according to claim 1, wherein one of the stimulation coding strategies uses adaptive stimulation pulse rates and another stimulation coding strategy uses constant stimulation rates.

7. The method according to claim 1, wherein the key feature value is a signal to noise ratio (SNR) of the input sound signal.

8. The method according to claim 1, wherein the key feature value is a direct to reverberation ratio (DRR) of the input sound signal.

9. The method according to claim 1, wherein the key feature value is envelope slope of the band pass envelope signals.

10. The method according to claim 1, wherein the key feature value is envelope peak of the band pass envelope signals.

11. The method according to claim 1, wherein the key feature value is envelope amplitude of the band pass envelope signals.

12. The method according to claim 1, wherein the one or more selected band pass signals is a single band pass signal.

13. The method according to claim 1, wherein the one or more selected band pass signals is a plurality of selected band pass signals.

14. The method according to claim 13, wherein an n of m strategy is used with the plurality of band pass signals.

15. The method according to claim 13, wherein the plurality of selected band pass signals comprises a dominant channel having a largest key feature value and a plurality of adjacent channels.

* * * * *